United States Patent
Chen

(10) Patent No.: US 10,842,664 B2
(45) Date of Patent: Nov. 24, 2020

(54) SKIN-LIKE CONDOMS HAVING ACTIVE INGREDIENTS TO ENHANCE A MALE ERECTION AND A FEMALE AROUSAL

(71) Applicant: ARIZONA BOARD OF REGENTS ON BEHALF OF ARIZONA STATE UNIVERSITY, Scottsdale, AZ (US)

(72) Inventor: Shengxi Chen, Chandler, AZ (US)

(73) Assignee: ARIZONA BOARD OF REGENTS ON BEHALF OF ARIZONA STATE UNIVERSITY, Scottsdale, AZ (US)

(*) Notice: Subject to any disclaimer, the term of this patent is extended or adjusted under 35 U.S.C. 154(b) by 107 days.

(21) Appl. No.: 15/771,377

(22) PCT Filed: Oct. 28, 2016

(86) PCT No.: PCT/US2016/059480
§ 371 (c)(1),
(2) Date: Apr. 26, 2018

(87) PCT Pub. No.: WO2017/075460
PCT Pub. Date: May 4, 2017

(65) Prior Publication Data
US 2018/0360647 A1  Dec. 20, 2018

Related U.S. Application Data

(60) Provisional application No. 62/248,196, filed on Oct. 29, 2015.

(51) Int. Cl.
| | |
|---|---|
| A61F 5/41 | (2006.01) |
| A61F 6/04 | (2006.01) |
| A61K 31/7056 | (2006.01) |
| A61K 33/00 | (2006.01) |
| A61K 9/00 | (2006.01) |
| B32B 27/04 | (2006.01) |
| C08K 3/20 | (2006.01) |
| B32B 27/40 | (2006.01) |
| A61K 9/70 | (2006.01) |

(52) U.S. Cl.
CPC .......... *A61F 6/04* (2013.01); *A61F 5/41* (2013.01); *A61K 9/0034* (2013.01); *A61K 9/7007* (2013.01); *A61K 31/7056* (2013.01); *A61K 33/00* (2013.01); *B32B 27/04* (2013.01); *B32B 27/40* (2013.01); *C08K 3/20* (2013.01)

(58) Field of Classification Search
CPC .......... A61F 6/04; A61F 5/41; A61K 9/0034; A61K 9/7007; A61K 31/7056; A61K 33/00; B32B 27/04; B32B 27/40; C08K 3/20
See application file for complete search history.

(56) References Cited

U.S. PATENT DOCUMENTS

| | | | |
|---|---|---|---|
| 4,829,991 A | | 5/1989 | Boeck |
| 5,137,032 A | * | 8/1992 | Harmon |
| 5,209,424 A | | 5/1993 | Shields et al. |
| 5,646,181 A | * | 8/1997 | Fung et al. |
| 6,007,836 A | * | 12/1999 | Denzer |
| 6,840,244 B2 | | 1/2005 | Kemp |
| 8,734,838 B2 | * | 5/2014 | Shirai |
| 2003/0147845 A1 | * | 8/2003 | Saavedra |
| 2003/0161975 A1 | * | 8/2003 | Lucas |
| 2008/0039682 A1 | | 2/2008 | Shioiri |
| 2008/0193489 A1 | * | 8/2008 | De Armond |

FOREIGN PATENT DOCUMENTS

| | | |
|---|---|---|
| CA | 2725428 A1 | 11/2009 |
| EP | 0524836 A1 | 1/1993 |
| WO | 2003072340 A1 | 9/2003 |
| WO | 2009134767 A1 | 11/2009 |
| WO | 2015068174 A2 | 5/2015 |

OTHER PUBLICATIONS

Beksinska, et al., "Female condom technology: new products and regulatory issues", Contraception 83(4), 316-321 (2011, available online 2010).
Chakrapani, et al., "V-PROLI/NO, a Prodrug of the Nitric Oxide Donor, PROLI-NO", Organic Letters 9(17), 3409-3412 (2007).
Farnham, et al., "Regulatory initiatives for natural latex allergy: US perspectives", Methods 27, 87-92 (2002).
Free, et al., "Relationship Between Condom Strength and Failure During Use", Contraception 22(1), 31-37 (1980).
Frezieres, et al., "Evaluation of the Efficacy of a Polyurethane Condom: Results from a Randomized, Controlled Clinical Trial", Family Planning Perspectives 31(2), 81-87 (1999).
Nandurdikar, et al., "Glycosulated PROLI/NO Derivatives as Nitric Oxide Prodrugs", Org. Lett. vol. 12, No. 1, pp. 56-59 (2010).
Patent Cooperation Treaty, International Searching Authority, International Preliminary Report on Patentability and Written Opinion for PCT/US2016/059480, 7 pages, dated May 1, 2018, opinion dated Mar. 17, 2017.
Patent Cooperation Treaty, International Searching Authority, International Search Report for PCT/US2016/059480, 3 pages, dated Mar. 17, 2017.
Planned Parenthood, "Allergic to Latex? You Can Still Have Safer Sex", Planned Parenthood Advocates of Arizona, <URL:http://blog.advocatesaz.org/2012/05/02/allergic-to-latex-you-can-still-have-safer-sex/> (2012).
Sangribsub, et al., "Hydrophobization of multilayered film containing layerby-layer assembled nanoparticle by Nation adsorption", Polymer Bulletin 53(5-6), 425-434 (2005).
White, et al., "Size Does Matter, When It Comes to Condoms", The Huffington Post, <URL:https://www.huffingtonpost.com/melissa-white/size-does-matter-when-it-comes-to-condoms_b_5907974.html> (2014).
Zhang, et al., "Effect of Gelatin Addition on Properties of Pullulan Films", Journal of Food Science, vol. 78 (2013).

* cited by examiner

*Primary Examiner* — Alma Pipic
(74) *Attorney, Agent, or Firm* — Viksnins Harris Padys Malen LLP

(57) ABSTRACT

A condom assembly includes at least one of a condom, patch or glove made of at least one of natural latex, synthetic latex or the mixture of natural latex and synthetic latex. The natural latex, synthetic latex or the mixture of natural latex and synthetic latex contain prodrugs of nitric oxide and/or other active ingredients.

10 Claims, 3 Drawing Sheets

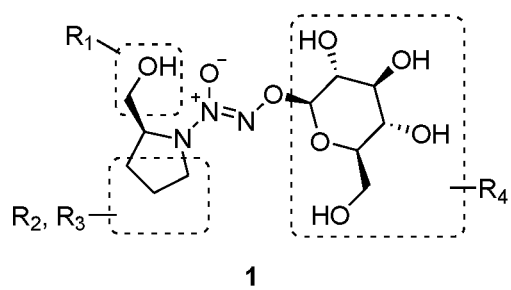
Figure 1
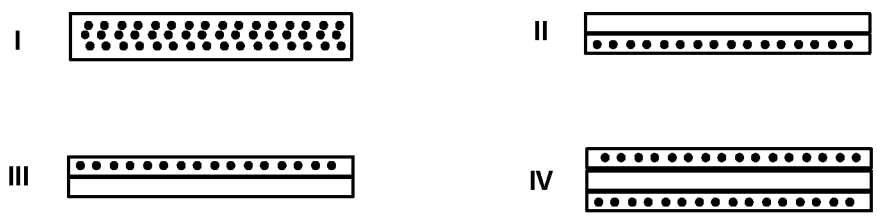
Condom layer made of formulation A: 
Condom layer made of formulation B: 
Pharmaceutical active ingredients: 
Figures 2I - IV

Figure 4

| Ingridient | Amount of ingredient (phr) | |
| --- | --- | --- |
| | A | B |
| Cariflex IR0401 latex | 100 | 100 |
| Sulfur | 1.5 | 1.5 |
| Zinc oxide (ZnO) | 0.5 | 0.5 |
| Zinc diethyl dithiocarbamate (ZDEC) | 1.0 | 1.0 |
| N,N'-Diphenylguanidine (DPG) | 1.0 | 1.0 |
| Butylated hydroxytoluene (BHT) | 2.0 | 2.0 |
| Sodium caseinate | 0.8 | 0.8 |
| Lecithin | 0.05 | - |
| Sodium carboxymethyl cellulose | 0.05 | - |
| D-glucosylated RPOLI/NO | 1.0 | - |

Figure 5

| Formulation | Contact angle (degrees) | Elongation (%) |
| --- | --- | --- |
| A | 18 | 1400 |
| B | 82 | 1050 |

SKIN-LIKE CONDOMS HAVING ACTIVE INGREDIENTS TO ENHANCE A MALE ERECTION AND A FEMALE AROUSAL

PRIORITY OF INVENTION

This application claims priority from U.S. Provisional Application No. 62/248,196, filed 29 Oct. 2015, which is hereby incorporated by reference in its entirety.

BACKGROUND

As a method of birth control, condoms have many advantages of low-cost, easy to use, and providing protection against numerous sexually transmitted infections (STIs). However, the drawbacks to more universal and consistent use of condoms are their tendencies to decrease pleasure and/or induce the loss of erection. The reason for these obstacles is that condoms are made from hydrophobic materials, such as latex, polyurethane, and polyisoprene. These hydrophobic materials are excluded from the human physiological environment, such as the surface of the skin. Thus, currently used condoms always cause the foreign body sensation to decrease pleasure and/or induce the loss of erection.

In addition, condoms are currently most often made from natural latex, which is derived from the sap of some plants. However, the use of latex condoms may cause allergic symptoms in people with an allergy to latex. In some normal people, the development of a latex allergy may be caused by the repeated use of latex condoms. To reduce the level of the allergy, some chemical synthesized materials, such as polyurethane and polyisoprene are used to make male condoms. A female condom was also developed, which is often made from nitrile. The condom made of natural latex has high quality of elastic properties. It can be stretched in excess of 800% before breaking and the tensile strength exceeds 30 MPa. A polyurethane condom has several better properties than latex condom: it does not have an odor; has a higher efficiency to transmit body heat; is less allergenic; has a longer storage life, and can be used with oil-based lubricants. However, a polyurethane condom has less elasticity than a latex condom. It is more likely to lose their shape, bunch up, break or slip than latex. Similar to a polyurethane condom, a nitrile condom has improved chemical resistance. However, it is less elastic than a latex condom too. A polyisoprene condom has less tensile strength than latex condom. However, it has the highest elongation before breaking (>1050%) and lower moduli, which result in increased softness. It also does not have an odor and has a higher efficiency to transmit body heat. In addition, it does not include proteins that cause latex allergies.

To benefit the erection, several patents have described condoms coated with active ingredients on their surface. For example, U.S. Pat. No. 4,829,991 describes a condom that coated with a vasodilator in its interior surface except at the closed and open end portions. The vasodilator (such as a nitroglycerine) transdermal coating on the surface of the condom contacts the skin of part of the shaft of the penis, after it is fitted onto a penis. The friction between the condom and the penis breaks the surface tension of the transdermal vasodilator coating and results in the gradual development of an erection.

U.S. Pat. No. 6,840,244 also describes a condom that can be used to deliver erectogenic compounds. In this patent, an erectogenic compound is coated on the interior surface of a condom in the closed end. The erectogenic compound is applied as a finely-divided form or as a film layer by the use of a solvent carrier, which is subsequently evaporated to leave the compound immobilised. In another way, the erectogenic compound is applied on the condom as a component of a composition, which is dispersed or dissolved in a gel carrier including a liquid medium and a thickening agent. The liquid medium is vegetable oil or a polyhydroxy-based medium. And the thickening agents include hectorite, jojoba oils, waxes or cellulose derivatives.

Int.'l Pat. Publication WO/2009/134767 describes a condom that affixes a low melt wax bead comprising an active ingredient on the interior surface of the condom in its tip. The bead comprises a polyethylene glycol-based wax or a natural wax mixed with polyethylene glycol. The wax softens in the range of 25-40° C. to substantially expose the active ingredients. Active ingredients include spermicides (e.g. nonoxynol-9), vasodilators (e.g. nitroglycerin, niacin, and sildenafil citrate) and male desensitizing agents (e.g. benzocaine). The exterior surface of the condom is free of the active ingredient.

It is an easily manipulated method to coat active ingredients on the surface of a condom described as above patents. However, the coating materials such as polyethylene glycol, jojoba oils, waxes or cellulose are very sticky, which are not pleasurable to users. In addition, these smooth adjuvant materials make condoms easily slipping off.

Recently, Int.'l Pat. Publication WO/2015/068174 describes a condom made of polymers mixed with graphene and its derivatives. The graphene and its derivatives are loaded with or without active ingredients to uniformly disperse into polymers. The mixed polymer is used to prepare condoms by dip casting methods. The pharmaceutical active ingredients in the nanocomposites of graphene and its derivatives are prepared for release during intercourse to increase the sexual pleasure. The condom prepared in this patent has higher mechanical strength and heat transfer. However, the active ingredients are trapped in the nanoparticles of graphene and its derivatives. Thus, the release rate and efficiency of the active ingredients are limit. In addition, the outer surface of the graphene nanoparticle is hydrophobic, which is not observably change the polarity of the surface of condom.

SUMMARY

A skin-like condom assembly is described herein including at least one of a condom, patch or glove made of at least one of natural latex, synthetic latex or the mixture of natural latex and synthetic latex, and natural latex, synthetic latex or the mixture of natural latex and synthetic latex contains prodrugs of nitric oxide and/or other active ingredients.

In one or more options, the skin-like condom, patch or glove is also described as 'skin mimic condom, patch or glove', 'skinny condom, patch or glove' or similar description.

In one or more options, the synthetic latex includes one or more of include polyurethane, polyisoprene, or nitrile latex.

A method is described herein including a method to prepare a condom, patch or glove made of natural latex or synthetic latex containing active ingredients in the whole entity or outside surface(s).

A compound is described herein including a compound having a prodrug of nitric oxide.

In a further option, the usage of prodrugs of nitric oxide to enhance a male erection and a female arousal, is described herein.

A condom assembly is described herein, including at least one of a condom, patch or glove used to deliver one or more other active ingredients selected from the group consisting of arginine, vasodilators or related compounds, including the nitrates, ergot alkaloids, long and short acting alpha-adrenoceptor blockers, anti-hypertenives, the prostaglandins and phosphodiesterase inhibitors.

The above active agents may be used either alone or in combination.

In one or more options, the condom, patch or glove may include or not include a hydrophilic adjuvant, such as lecithin and its analogues, polysaccharide analogues, or proteins.

In one or more embodiments, a condom, patch or glove is made of natural latex, synthetic latex or the mixture of natural latex and synthetic latex containing extra protein(s).

In one or more embodiments, a condom, patch or glove is made of natural latex or synthetic latex containing protein(s) or phospholipid(s).

In one or more embodiments, a condom, patch or glove is made of natural latex or synthetic latex containing protein(s) and/or polysaccharide.

In one or more embodiments, a condom, patch or glove is made of natural latex or synthetic latex containing protein(s), phospholipid(s), and polysaccharide(s).

In one or more embodiments, synthetic latexes include polyurethane, polyisoprene or nitrile latex.

In one or more embodiments, proteins are derivable from caseinate (Na, K, $NH_4$, Mg, Ca, Zn), extraction of milk, soybeans, peanuts, corn and other natural objects.

In one or more embodiments, phospholipids include lecithin, phosphatidic acid, phosphatidylethanolamine, phosphatidylserine, phosphatidylinositol, phosphatidylinositol phosphate, ceramide phosphorylcholine, ceramide phosphorylethanolamine, or ceramide phosphoryllipid.

In one or more embodiments, polysaccharides include starch, glycogen, cellulose, chitin, callose, laminarin, chrysolaminarin, xylan, arabinoxylan, mannan, fucoidan and galactomannan.

BRIEF DESCRIPTION OF THE DRAWINGS

FIG. 1 illustrates compound 1 and its potential modified sites in accordance with one or more embodiments.

FIG. 2I illustrates a cross-section of a condom layer of formulation A in accordance with one or more embodiments.

FIG. 2II illustrates a cross-section of a condom layer of formulation A and formulation B in accordance with one or more embodiments.

FIG. 2III illustrates a cross-section of a condom layer of formulation A and formulation B in accordance with one or more embodiments.

FIG. 2IV illustrates a cross-section of a condom layer of formulation A and formulation B in accordance with one or more embodiments.

FIG. 4 illustrates formulations for polyisoprene latex.

FIG. 5 illustrates a table showing properties of condom prepared using formulations of A and B.

DETAILED DESCRIPTION

Figure 3:
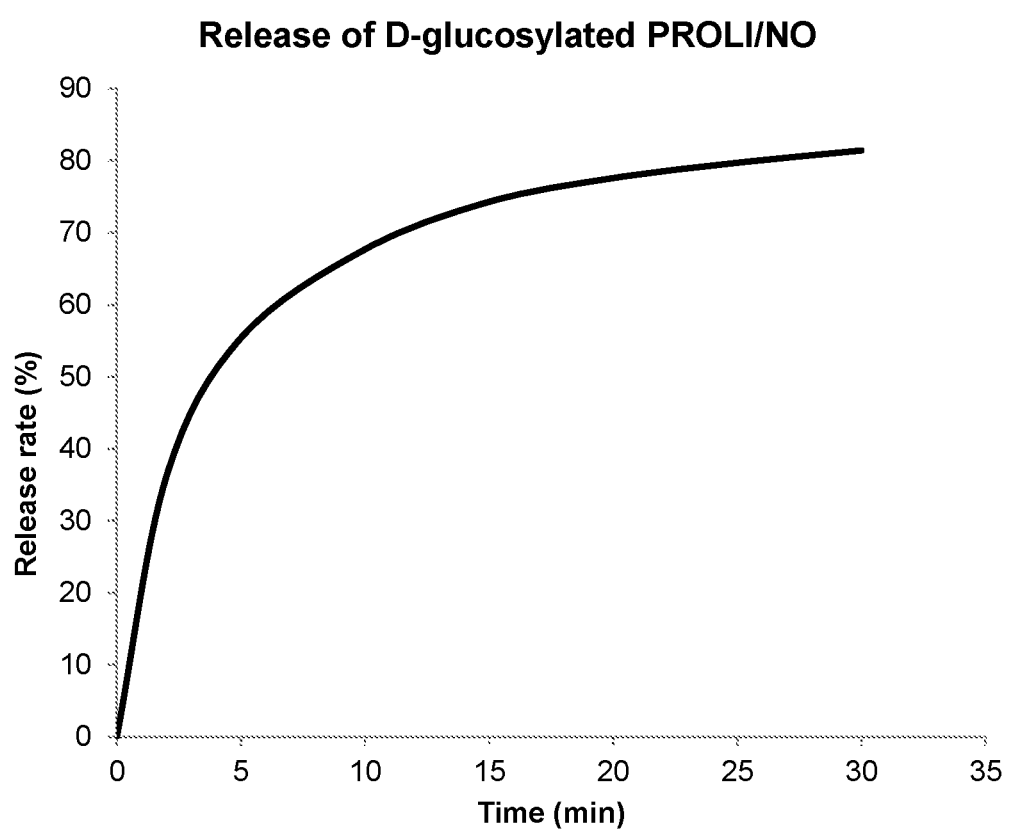
FIG. 3 illustrates a chart showing the time-dependent release of D-glucosylated PROLI/NO from condom I.

A skin-like condom containing pharmaceutical active ingredients that uniformly distribute on the surface of latex particles is described herein. The term condom and skin-like condom includes a condom, patch, or glove.

Condoms are prepared using polyisoprene latex containing prodrugs of nitric oxide. The prodrugs of nitric oxide will be released from these condoms; transported into smooth muscle cells; decomposed to nitric oxide. The nitric oxide activates the erection and female arousal.

A condom assembly is described herein, including at least one of a condom, patch or glove used to deliver other active ingredients selected from the group consisting of arginine, vasodilators or related compounds, including the nitrates, ergot alkaloids, long and short acting alpha-adrenoceptor blockers, anti-hypertenives, the prostaglandins or phosphodiesterase inhibitors. The above active agents may be used either alone or in combination.

In one or more options, the condom, patch or glove may include or not include a hydrophilic adjuvant, such as lecithin and its analogues, polysaccharide analogues, or proteins.

In one or more embodiments, a condom, patch or glove is made of natural latex, synthetic latex or the mixture of natural latex and synthetic latex containing extra protein(s).

In one or more embodiments, a condom, patch or glove is made of natural latex or synthetic latex containing protein(s) and phospholipid(s).

In one or more embodiments, a condom, patch or glove is made of natural latex or synthetic latex containing protein(s) and polysaccharide.

In one or more embodiments, a condom, patch or glove is made of natural latex or synthetic latex containing protein(s), phospholipid(s), and polysaccharide(s).

In one or more embodiments, synthetic latexes include polyurethane, polyisoprene and nitrile latex.

In one or more embodiments, proteins are derivable from caseinate (Na, K, $NH_4$, Mg, Ca, Zn), extraction of milk, soybeans, peanuts, corn and other natural objects.

In one or more embodiments, phospholipids include lecithin, phosphatidic acid, phosphatidylethanolamine, phosphatidylserine, phosphatidylinositol, phosphatidylinositol phosphate, ceramide phosphorylcholine, ceramide phosphorylethanolamine, or ceramide phosphoryllipid.

In one or more embodiments, polysaccharides include starch, glycogen, cellulose, chitin, callose, laminarin, chrysolaminarin, xylan, arabinoxylan, mannan, fucoidan or galactomannan.

The active ingredient has higher hydrophilic property than latex particle. Thus the novel condom containing pharmaceutical active ingredients on the surface of latex particles has increased polarity and electroconductivity. The condom itself provides increased pleasure to users since its surface is friendly to human skin. The active ingredient releases out promptly and continuously, which provide constant enhancement for the erection of penis. Some active ingredients (e.g. nitric oxide derivatives) can also increase female arousal, which provide increased pleasure for both partners. In addition, the active ingredient(s) can increase the mechanical strength and heat transfer ability of the condom. The novel condoms containing pharmaceutical active ingredients on the surface of latex particles are prepared to enhance a male erection and a female arousal, increase pleasure for both partners, prevent pregnancy and sexually transmitted diseases.

The present invention also provides a novel prodrug of nitric oxide, D-glucosylated PROLI/NO (1, FIG. 1). This prodrug and its derivatives may arouse and enhance the erection for male, and may also arouse and enhance sexual excitement for female.

The disadvantage of currently used condoms is the decreasing pleasure and/or inducing the loss of erection, since they were made of hydrophobic materials that are excluded from the human physiological environment, such as the surface of the skin. In this invention a pharmaceutical active ingredient is uniformly distribute on the surface of latex particles to increase the polarity and the mechanical strength of condom, which is friendly to human skin to increase pleasure for both partners. In addition, the active ingredient releases out from the condom, provides enhancement for the erection of penis and female arousal, results in more pleasure to both partners.

One embodiment provides a condom (FIG. 2I) made of polyisoprene latex composition comprising D-glucosylated PROLI/NO (1), which is a prodrug of nitric oxide. The formulation (A) of this polyisoprene latex contains 1.0 phr of D-glucosylated PROLI/NO and small amount of hydrophilic adjuvant. As a control, another formulation (B) just contains polyisoprene latex without D-glucosylated PROLI/NO and hydrophilic adjuvant. The condom made from formulation A has a much higher hydrophily and litter higher mechanical strength than that of formulation B. The contact angle ($\theta$) of 5 μL water on the surface of polyisoprene condom made from formulation A is 18 degrees, and the elongation is 1400%. Comparatively, the contact angle ($\theta$) of 5 μL water on the surface of polyisoprene condom made from formulation B is 82 degrees, and its elongation is 1050%.

The second embodiment provides a condom (FIG. 2II) making up of formulation (A) of latex on the internal side and formulation (B) on the external side of condom. The third embodiment provides a condom (FIG. 2III) making up of formulation (A) of latex on the external side and formulation (B) on the internal side of condom.

The fourth embodiment provides a condom (FIG. 2IV) making up of formulation (A) of latex on the both sides and formulation (B) in the middle layer of condom.

The latex in this invention may use natural latex, synthetic latex or the mixture of natural latex and synthetic latex. The synthetic latexes include polyurethane, polyisoprene and nitrile latex. The forms of the latex to delivery pharmaceutical active ingredient(s) include condom, patch or glove.

The pharmaceutical active ingredients for enhancing a male erection and a female arousal include but not limit to prodrugs of nitric oxide, such as glucosylated PROLI/NO (1) and its analogues: R1 includes but not limit to hydrogen (H), hydroxymethyl (—CH$_2$OH), aminomethyl (—CH$_2$NH$_2$) and its derivatives, carboxyl (—COOH) and its derivatives, carboxamide (—CONH$_2$) and its derivatives. R2 and R3 may be two separate aliphatic hydrocarbon chains or aromatic hydrocarbons chains; or forms a ring which includes 3 to 15 atoms. R4 includes but not limit to aliphatic hydrocarbon, aromatic hydrocarbons, galactose, glucose, mannose, N-acetylglucosamine and their O-acetyl derivatives.

The condom, patch or glove may be used to delivery other kinds of active ingredients, such as arginine, vasodilators or related compounds, including the nitrates, ergot alkaloids, long and short acting alpha-adrenoceptor blockers, anti-hypertenives, the prostaglandins and phosphodiesterase inhibitors Suitable nitrates include but not limit to amyl nitrate, erythrityl tetranitrate, isosorbide dinitrate, nitro-glycerine, sodium nitroprusside, linsidomine chlorydrate ("SIN-1"), molsidomine, S-nitroso-N-acetyl-d,l-penicillamine ("SNAP"), S-nitroso-N-glutathione ("SNO-GLU"), S-nitroso-N-cysteine, and diazenium diolates ("NONOates").

Useful prostaglandins include but not limit to PGA$_1$, PGB$_1$, PGE$_0$, PGE$_1$, PGF$_1$alpha, 19-hydroxy-PGA$_1$, 19-hydroxy-PGB$_1$, PGA$_2$, PGB$_2$, PGE2, 19-hydroxy-PGA$_2$, 19-hydroxy-PGB$_2$, PGE$_3$, PGF$_3$alpha, carboprost tromethamine, dinoprostone, dinoprost tromethamine, gemeprost, lipoprost, metenoprost, sulprostone and tiaprost.

Suitable alpha-adrenoceptor blockers include but not limit to alfuzosin, dibenamine, doxazosin, indoramin, phenoxybenzamine, phentolamine, prazosin, tamsulosin, terazosin, trimazosin, and tolazoline.

Useful ergot alkaloids include but not limit to acetergamine, bromerguride, brazergoline, cianergoline, disulergine, delorgotrile, ergonovine maleate, etisulergine, ergotamine tartrate, lergotrile, lysergide, metergoline, metergotamine, mesulergine, nicergoline, pergolide, proterguride, propisergide and terguride.

Suitable type III phosphodiesterase inhibitors include but not limit to amirinone, anergrelide, bemoradan, cilostamide, cilostazol, enoximone, imazodan, indolidan, isomazole, 5-methyl-imazodan, lixazinone, milrinone, pimobendan, piroximone, siguazodan, trequinsin, vesnarinone, ICI1118233, SKF-94120 and SKF-95654.

Usable type IV phosphodiesterase inhibitors include but not limit to etazolate, nitraquazone and nitraquazone derivatives, rolipram and rolipram derivatives, xanthine and xanthine derivatives.

Suitable type V phospodiesterase inhibitors include but not limit to sildenafil, tadalafil, vardenafil, and zaprinast.

Other compounds include IBMX, papaverine, pentoxifylline, theophylline, cyclandelate, chloromazine, haloperidol, isoxsuprine, nimodipine, pinacidil, and trazodone, as well as anti-hyertensive agents including minoxidil, hydralazine and diazoxide.

The above active agents may be used either alone or in combination.

The condom, patch or glove may include or not include a hydrophilic adjuvant, such as lecithin and its analogues, polysaccharide analogues, and proteins.

The active ingredient releases out promptly and continuously from the condoms. In a release assay, around 55% of D-glucosylated PROLI/NO is released into water from condom in 5 min (FIG. 3). And 81% of this prodrug is released out in 30 min. The continuous release of active ingredient provides constant enhancement of pleasure for both partners.

EXAMPLES

Example 1

The tetra-acetyl-D-glucosylated PROLI/NO was prepared as reported procedure. To a solution of tetra-acetyl-D-glucosylated PROLI/NO (316 mg, 0.625 mmol) in 15 mL of anhydrous methanol was added 25% NaOMe in methanol (20 μL, 0.09 mmol). The reaction mixture was stirred at rt for 2 h. The crude product was purified by flash column chromatography (9:1 CH$_2$Cl$_2$/MeOH eluent) to give 1 (125 mg, 62%) as a white solid. H NMR (400 MHz, CD$_3$OD) δ: 1.28-2.06 (m, 4H), 3.28-3.46 (m, 4H), 3.50-3.72 (m, 5H), 3.83 (d, J=1 Hz, 1H), 4.06-4.09 (m, 1H), 4.83 (s, 5H), 4.96 (d, J=8 Hz, 1H); $^{13}$C NMR (CD$_3$OD) δ: 22.3, 26.2, 52.2, 61.0, 63.1, 69.6, 71.7, 76.4, 77.1, 103.3.

14.12; MALDI: m/z=346 for (M+Na)$^+$

Example 2

The formulation (A) of polyisoprene latex is prepared by mixing 100 phr of compounded Cariflex IR0401 latex (Kraton Polymers U.S. LLC) with 1.0 phr of D-glucosylated PROLI/NO. The compounded latex is stirred at room temperature for 2-8 h and centrifuged for 5 min. Then smooth glass formers are dipped in the latex suspension for 1 min and dried at 60° C. for 5 min.

The dipping and drying procedures are repeated three to four times. Finally, the condoms are cured at 130° C. for 15 min.

Example 3

The formulation (B) of polyisoprene latex is prepared by mixing the compounded Cariflex IR0401 latex (Kraton Polymers U.S. LLC) without D-glucosylated PROLI/NO and hydrophilic adjuvant. The compounded latex is stirred at room temperature for 2-8 h and centrifuged for 5 min.

Then smooth glass formers are dipped in the formulation (A) of latex suspension for 1 min and dried at 60° C. for 5 min. This procedure is repeated one time. Then the formers coated with the formulation (A) of latex are dipped in the formulation (B) of latex suspension for 1 min and dried at 60° C. for 5 min. The latter dipping and drying procedures are repeated one time. Finally, the condoms are cured at 130° C. for 15 min.

Example 4

The smooth glass formers are dipped in the formulation (B) of latex suspension for 1 min and dried at 60° C. for 5 min. This procedure is repeated one time. Then the formers coated with the formulation (B) of latex are dipped in the formulation (A) of latex suspension for 1 min and dried at 60° C. for 5 min. The latter dipping and drying procedures are repeated one time. Finally, the condoms are cured at 130° C. for 15 min.

Example 5

The smooth glass formers are dipped in the formulation (A) of latex suspension for 1 min and dried at 60° C. for 5 min. Then the formers coated with the formulation (A) of latex are dipped in the formulation (B) of latex suspension for 1 min and dried at 60° C. for 5 min. The latter dipping and drying procedures are repeated one time. Then the formers are dipped again in the formulation (A) of latex suspension for 1 min and dried at 60° C. for 5 min. Finally, the condoms are cured at 130° C. for 15 min.

Example 6

One condom containing 7 mg of D-glucosylated PROLI/NO is suspended in 20 mL of pure water. A 100-μL of sample is taken out at 2 min, 5 min, 10 min, 15 min, 20 min, 25 min and 30 min. The UV absorption is measured at 255 nm. As a control, a condom without the D-glucosylated PROLI/NO is also treated as the same way. The release amount is calculated based on the UV absorption of pure D-glucosylated PROLI/NO.

Example 7

In one or more embodiments, a skin-like condom is described herein, which mimics the membrane of living cells to increase pleasure. The human cell membrane is a biological membrane that surrounds the cytoplasm of living cells. It involves in a variety of cellular processes such as ion conductivity, cell adhesion and cell communication. Cell membrane consists of a lipid bilayer with embedded proteins. The glycosylation of the surface of embedded proteins increase the hydrophily of the membrane. In this study, we added a D-glucosylated PROLI/NO and several hydrophilic adjuvants into the polyisoprene latex and used this mixture to prepare condoms. The hydrophilic compounds located at the surface of the polyisoprene condom to mimic the surface of cell membrane for higher hydrophily and increased sensation.

Condoms have been prepared with two different formulations of polyisoprene latex (FIG. 4). Both polyisoprene latex formulations contain Cariflex IR0401 latex (Kraton Polymers U.S LLC); bridging agent (sulfur); activator (ZnO); accelerators (ZDEC and DPG); and anti-oxidant (BHT). Besides these uniform agents, formulation A contains D-glucosylated PROLI/NO, sodium caseinate, lecithin and sodium carboxymethyl cellulose; formulation B only contains a sodium caseinate.

The contact angle (θ) of 5 μL water on the surface of polyisoprene condom made from formulation A is 18 degrees (FIG. 5), and the elongation is 1400%. The active ingredients in latex dramatically increases the hydrophily and slightly increases the flexibility of the condom. The contact angle (θ) of 5 μL water on the surface of polyisoprene condom made from formulation B is 82 degrees, and the elongation is 1050%.

In summary, we prepared skin-like condoms using two formulations of polyisoprene latex to mimic the membrane of living cells. These condoms have increased hydrophily and flexibility compared to condoms that made from natural latex. The condoms prepared in this study will increase pleasure and decrease the rate of latex allergies.

The present invention provides a novel condom containing pharmaceutical active ingredients that uniformly distribute on the surface of latex particles. The active ingredient has higher hydrophilic property than latex particle. Thus the novel condom containing pharmaceutical active ingredients on the surface of latex particles has increased polarity and electroconductivity. The condom itself provides increased pleasure to users since its surface is friendly to human skin. The active ingredient releases out promptly and continuously, which provide constant enhancement for the erection of penis. Some active ingredients (e.g. nitric oxide derivatives) can also increase female arousal, which provide increased pleasure for both partners. In addition, the active ingredient(s) can increase the mechanical strength and heat transfer ability of the condom. The novel condoms containing pharmaceutical active ingredients on the surface of latex particles are prepared to enhance a male erection and, a female arousal, increase pleasure for both partners, prevent pregnancy and sexually transmitted diseases. The present invention also provides a novel prodrug of nitric oxide, D-glucosylated PROLI/NO. This prodrug and its derivatives may arouse and enhance the erection for male, and may also arouse and enhance sexual excitement for female.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A condom assembly comprising:
   at least one of a condom made of at least one of a natural latex, a synthetic latex or a mixture of the natural latex and the synthetic latex; and
   the at least one of the natural latex, the synthetic latex or the mixture of the natural latex and the synthetic latex containing a compound of Formula 1

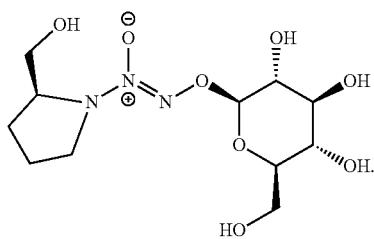

Formula 1

2. The condom assembly as recited in claim 1, wherein the synthetic latex, the mixture of the natural latex and the synthetic latex, the synthetic latex containing the compound of Formula 1, or the mixture of the natural latex and the synthetic latex containing the compound of Formula 1, each comprises polyurethane, polyisoprene, or nitrile latex.

3. The condom assembly as recited in claim 1, wherein the condom comprises a hydrophilic adjuvant.

4. The condom assembly as recited in claim 1, wherein the condom further comprises one or more proteins.

5. The condom assembly as recited in claim 1, wherein the condom comprises one or more proteins and one or more phospholipids.

6. The condom assembly as recited in claim 1, wherein the condom comprises one or more proteins and one or more polysaccharides.

7. The condom assembly as recited in claim 1, wherein the condom comprises one or more proteins, one or more phospholipids, and one or more polysaccharides.

8. The condom assembly as recited in claim 4, wherein the one or more proteins are derived from caseinate, soybeans, peanuts, or corn.

9. The condom assembly as recited in claim 5, wherein the one or more phospholipids comprise lecithin, phosphatidic acid, phosphatidylethanolamine, phosphatidylserine, phosphatidylinositol, phosphatidylinositol phosphate, ceramide phosphorylcholine, ceramide phosphorylethanolamine, or ceramide phosphoryllipid.

10. The condom assembly as recited in claim 6, wherein the one or more polysaccharides include starch, glycogen, cellulose, chitin, callose, laminarin, chrysolaminarin, xylan, arabinoxylan, mannan, fucoidan, or galactomannan.

* * * * *